US00PP11992P2

(12) United States Plant Patent
Jones et al.

(10) Patent No.: US PP11,992 P2
(45) Date of Patent: Jul. 17, 2001

(54) APPLE TREE 'JOBURN'

(76) Inventors: Graeme Jones; Karen Jones, both of 115 Thompson Road R.D. 2, Hastings (NZ)

( * ) Notice: Subject to any disclaimer, the term of this patent is extended or adjusted under 35 U.S.C. 154(b) by 0 days.

(21) Appl. No.: 08/979,898

(22) Filed: Nov. 26, 1997

Related U.S. Application Data

(63) Continuation of application No. 08/690,294, filed on Jul. 26, 1996, now abandoned.

(51) Int. Cl.[7] ..... A01H 5/00
(52) U.S. Cl. ..... Plt./161
(58) Field of Search ..... Plt./34.1, 161

(56) References Cited

U.S. PATENT DOCUMENTS

P.P. 7,526 * 5/1991 Hill et al. ..... Plt./34.1

OTHER PUBLICATIONS

GTITM UPOVROM listing for NZPBRAPP067, for 'Joburn' filed: Mar. 2, 1990; published: Apr. 14, 1990.*

* cited by examiner

*Primary Examiner*—Howard J. Locker
(74) *Attorney, Agent, or Firm*—Christie, Parker & Hale, LLP

(57) ABSTRACT

A new and distinct variety of apple tree is a limb mutation of the 'Braeburn' variety (an unpatented New Zealand variety), with the fruit of the new variety characterized by a much more highly colored red striped and blushed appearance as compared to 'Braeburn'. The new variety has been named 'Joburn'.

2 Drawing Sheets

SUMMARY OF THE INVENTION

'Braeburn' is an unpatented variety of apple commonly grown commercially in New Zealand, and increasingly in other part of the world. The fruit of 'Braeburn' is typically striped, with coverage of between 40% to 50% orange-red stripes. A number of sports or mutations have arisen on trees of 'Braeburn' which are similar in habit and yield to 'Braeburn,' but which have different skin coloration. One such sport is the variety 'Hidala' (U.S. Plant Pat. No. 7,526), which has skin color of orange-red stripes over about 50% to 70% of the fruit surface; another is 'Mariri Red' (U.S. Plant Pat. No. 11,604), which has approximately 100% coverage of red blush. Such sports with increased red coloration are seen to have some commercial advantage over 'Braeburn'.

A limb mutation on a apple tree of variety Braeburn (an unpatented New Zealand cultivar) exhibited highly colored red striped and blushed fruit compared to its parental variety. The new variety has been asexually reproduced and named Joburn.

The mutation was noticed because 2 apples on a spur had higher red coloration than the rest of the crop on the tree.

The spur was left to grow for 2 seasons, and in August 1987 graftwood was taken and used to top-graft an existing tree on the owners property in Thompson Rd, Hastings. In Spring 1988 budwood was taken from the top-grafted tree to produce 200 second generation trees on M793 rootstock. These trees were planted in winter 1990.

Asexual propagation by budding and grafting in Hawkes Bay, New Zealand, has shown that the unique combination of plant characteristics and distinctive coloration characteristics come true to form and are established and faithfully transmitted through succeeding generations.

DETAILED DESCRIPTION OF THE DISCLOSURE

Figure 1:
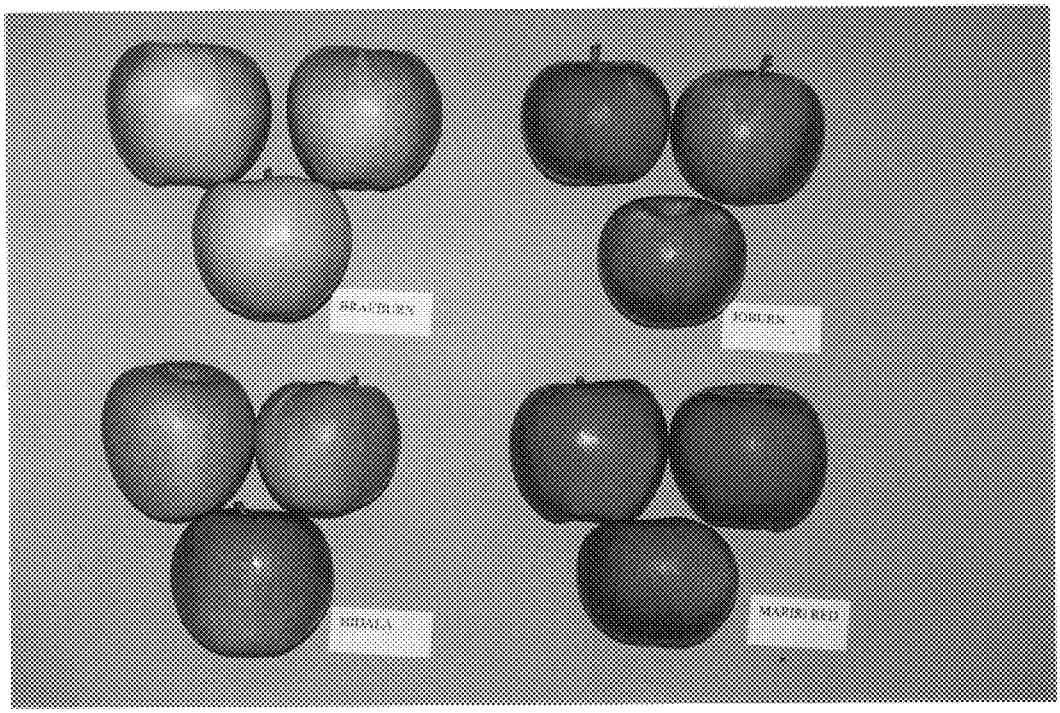
FIG. 1 shows three apples of the varieties 'Braeburn,' 'Joburn,' 'Hidala' and 'Mariri Red' in side views. 'Joburn' has dark red stripes over an underlying dark red blush typically covering between 75% to 100% of the fruit surface.
Figure 2:
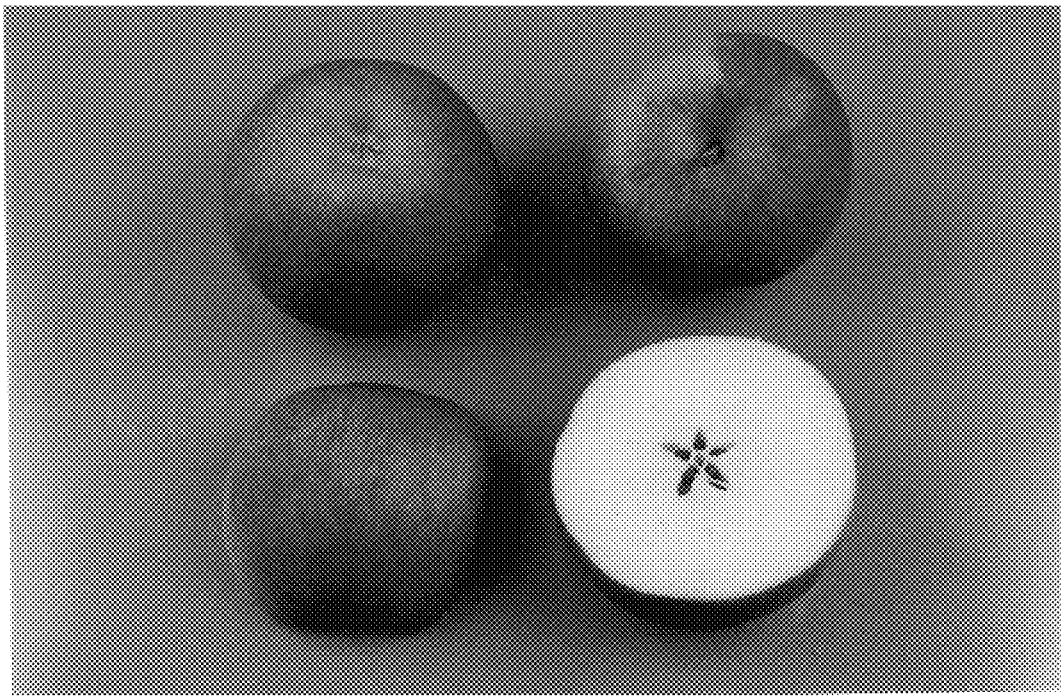
FIG. 2 shows 'Joburn' apple in cross-section.

The Joburn is a variety of domestic apple tree (*Malus domestica*).

The following is a detailed description of the new variety with color terminology in accordance with the 1986 Edition of The Royal Horticultural Society Colour Chart (R.H.S.C.C.).

The trees described were planted in 1988 on M793 rootstock. Observations on trees and fruit were made in Autumn 1995.

Tree: Medium to medium — weak vigor on MM106 rootstock. Size of mature trees on MM106 rootstock of about 3.5 m. high by about 2.0 m. wide. Not substantially different from comparative varieties 'Mariri Red,' 'Hidala' or 'Braeburn.' The bearing characteristics are not substantially different from the comparative varieties 'Mariri Red', 'Hidala' or 'Braeburn.' That is, unthinned trees tend to bear biennially, but trees thinned and cropped in a commercial manner are not biennial. Typical commercial production in New Zealand from trees on MM106 rootstock is about 100 kg. to 150 kg per tree. Predominance of bearing is on spurs on older wood, and on axillary buds on one-year-old wood.

Branches: Medium thick; smooth; angle of major scaffold branches — typically about 60° above the horizontal.

*Lenticels on bark.*—Few in number, about 5 per square cm. on one-year-old branches; round to ovate in shape; near 156D in color.

*Leaf petioles.*—Typical length about 28 mm.

*Leaf color.*—Upper surface near 137A, lower surface near 138B.

Leaves: Upward pose; medium glossiness of upper side; medium pubescence on lower side, medium petiole length.

*Size.*—Small to medium.

Flowers: Early-season flowering, medium size; flat shape, margin of petals touching. Color of petals soon after opening is Red-Purple Group near 63B.

*Time of flowering.*—'Joburn' showed about 90% full bloom on about Oct. 7, 1997, at Havelock North, New Zealand.

*Suitable pollenisers.*—Any diploid apple variety flowering at a similar time, apart from 'Braeburn' or sports of 'Braeburn'.

*Bloom diameter.*—Not substantially different from comparative varieties 'Mariri Red,' 'Hidala' or 'Braeburn.'

Fruit:

*Ripening.*—Late season. Over the period late-March to early-April in Hastings, Hawkes Bay. In Hawkes Bay, 'Joburn' ripens about one-week after 'Braeburn' and 'Hidala,' at the same time as 'Mariri Red,' as determined by measurements of background color, flesh firmness, titratable acidity, soluble solids (sugars) and starch levels in the fruit. This has been documented in the following independent reports, among others:

*Fenemor, D (1996). Sports comparison trial.*—Braeburn Sports Report PH95/G/N-2, to ENZA New Zealand (International) ltd.

*Bensley, R (1996). Braeburn sport comparison trial.*—Report PH95/7/H to ENZA New Zealand (International) Ltd.

Typical fruit size at maturity on trees thinned in a commercial manner is about 76 mm. maximum width and about 60 mm in height.

*Shape.*—Globose conical, asymmetric in side view, ribbing present, very weak crowning at distil end.

*Stalk cavity.*—Medium depth with medium width.

*Eye basin.*—Shallow-medium depth, medium width (similar to Golden Delicious).

*Stem thickness.*—Medium. Not substantially different from comparative varieties 'Mariri Red,' 'Hidala' or 'Braeburn.'

*Stem length.*—About 18 mm.

*Calyx.*—Partially open, medium size. Not substantially different from comparative varieties 'Mariri Red,' 'Hidala' or 'Braeburn.'

Sepals:

*Size.*—Short-medium length.

*Spacing of sepals at base.*—Touching.

Skin: Medium to thick; smooth.

*Bloom of skin.*—Absent.

*Greasiness of skin.*—Absent.

*Cracking tendency of skin.*—Absent.

*Coloration.*—The development of color begins earlier than 'Braeburn,' and the color of the mature fruit is greater than that of 'Braeburn.'

*Ground color.*—Near 150C.

*Over-color.*—Dark red stripes over an underlying dark red blush, typically covering between 75% to 100% of the fruit surface. The color of both the stripes and blush is Greyed-Purple Group near 185A, but differ in intensity of color. Fruit of high maturity and fruit which is grown on places in the tree which are more exposed to sunlight have more red coloration and that coloration is more intense. On some fruit the intensity of the blush is such that it is equivalent to the stripes, and the stripes are difficult to distinguish.

*Lenticels.*—Small and inconspicuous.

*Russet.*—Low to medium around step cavity.

*Propensity to russet.*—Low.

Flesh: Juicy, medium firmness, cream, Yellow-Green Group near 150D weak browning of flesh (one hour after cutting with stainless steel knife).

*Texture.*—Medium (as for Cox's Orange Pippin).

Core:

*Distinctness of core line in cross section (median through locules).*—Medium to strong.

*Aperture of locules in cross section.*—Closed.

Seeds: Medium sized; Greyed-Orange Group near 175B.

Use: Dessert.

*Keeping quality.*—Very good, with fruit storing in excess of about 100 days in cool storage (at 1° C.) with few storage disorders.

*Disease resistance.*—Not substantially different from comparative varieties 'Mariri Red,' 'Hidala' or 'Braeburn.'

Susceptibility to:

*Insects.*—Medium.

*Diseases.*—Medium.

Differences from similar varieties: Compared to Braeburn and Hidala (U.S. Plant Pat. No. 7,526).

Joburn has: Higher amount of red coloration. A red blush under striping on exposed areas of the fruit. More consistent coverage of red color, especially associated with the shaded side of the fruit compared with Braeburn and Hidala. Earlier development of red color. Joburn ripens up to week earlier than Braeburn and Hidala. Joburn has a shortened harvest period compared to Braeburn and Hidala.

Table 1 shows a comparison between 'Joburn,' 'Mariri Red' (U.S. Plant Pat. No. 11,604), 'Hidala' and 'Braeburn.'

TABLE 1

| | VARIETY COMPARISONS | | | |
|---|---|---|---|---|
| | JOBURN | MARIRI RED | HIDALA | BRAEBURN |
| Overcolor (RHS 1986) | near 185A | near 187B | near 179A | near 179A |
| Color coverage | between 75% to 100% | about 100% | between 50% to 70% | between 40% to 50% |
| Color pattern | stripes over blush | blushed | stripes over blush | stripes over blush |
| Time of ripeness | about 7 days after 'Braeburn' | about 7 days after 'Braeburn' | Same as 'Braeburn' | |
| Time of coloration | Earlier than 'Braeburn' | Earlier than 'Braeburn' | Same as 'Braeburn' | |

We claim:

1. A new and distinct variety of apple tree which is a mutation of the Braeburn variety substantially shown and described, characterised by dark-red striping and blush which extends over the entire surface of the fruit.

* * * * *